United States Patent [19]

Konrad et al.

[11] Patent Number: 4,886,516

[45] Date of Patent: Dec. 12, 1989

[54] DIAMINOTETRAFLUOROETHOXYBEN-ZENES, PROCESS FOR PRODUCING SAME AND HAIR COLORING AGENTS CONTAINING SAME

[75] Inventors: Eugen Konrad, Darmstadt; Thomas Clausen, Alsbach, both of Fed. Rep. of Germany

[73] Assignee: Wella Aktiengesellschaft, Darmstadt, Fed. Rep. of Germany

[21] Appl. No.: 258,041

[22] Filed: Oct. 13, 1988

Related U.S. Application Data

[63] Continuation of Ser. No. 758,203, Jul. 22, 1985, abandoned.

[30] Foreign Application Priority Data

Aug. 18, 1984 [DE] Fed. Rep. of Germany ....... 3430513

[51] Int. Cl.$^4$ .......................... C07C 85/11; A61K 7/13
[52] U.S. Cl. ............................................ 8/408; 8/411; 8/416; 564/422
[58] Field of Search .................... 564/422; 8/408, 411, 8/416

[56] References Cited

U.S. PATENT DOCUMENTS 4,125,367 11/1978 Bugaut et al. ........................... 8/408
4,171,203 10/1979 Rose et al. ........................... 564/443
4,543,425 9/1985 Konrad et al. ...................... 564/442

FOREIGN PATENT DOCUMENTS 537504 8/1977 U.S.S.R. .

OTHER PUBLICATIONS

B. N. Ames, J. MacCann and E. Yamasaki, Mut. Res. 31 347–373 (1975).

Primary Examiner—Mukund J. Shah
Assistant Examiner—Frederick Tsung
Attorney, Agent, or Firm—Michael J. Striker

[57] ABSTRACT

Tetrafluoroethoxybenzenes, and their acid addition salts, of the general formula:

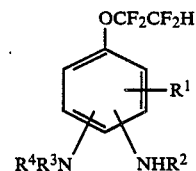

in which $R^1$ may represent hydrogen or an alkyl having from 1 to 4 carbon atoms and $R^2$, $R^3$ and $R^4$ represent one or more of the same or different substituents selected from hydrogen, an alkyl having 1 to 4 carbon atoms or mono- or dihydroxyalkyls having 1 to 4 carbon atoms, provided that the amino groups are situated relative to one another in an ortho- or meta- position and $R^1$, $R^2$, $R^3$ and $R^4$ do not simultaneously represent hydrogen when the amino groups are arranged in a 2,4-position. The compounds of the invention, along with 2,4-diaminotetrafluoroethoxybenzene, are useful as coupler components in oxidative hair coloring agents. A process for making the compounds, as well as a separate process for making the mono-N-β-hydroxyethyl compounds, is provided.

9 Claims, No Drawings

DIAMINOTETRAFLUOROETHOXYBENZENES, PROCESS FOR PRODUCING SAME AND HAIR COLORING AGENTS CONTAINING SAME

This application is a continuation of application Ser. No. 758,203, filed July 22, 1985 now abandoned.

The present invention relates to new diaminobenzene derivatives containing a tetrafluoroethoxy group, their preparation and application as components of agents for the oxidative coloring of hair in which known developing components are employed along with diaminotetrafluoroethoxybenzenes as coupling components.

Oxidizing coloring materials are known to be of substantial importance in the coloring of hair. The coloring is effected by means of the reaction of certain developer substances with certain coupler substances in the presence of a suitable oxidizing agent.

The preferred coupler substances currently being used are m-phenylenediamine and its derivatives, e.g., 2,4-diaminoanisol, 2,4-diaminophenetol and 2-amino-4-(β-hydroxyethyl)aminoanisol as blue couplers: α-napthol, m-aminophenol and 5-amino-o-cresol as red couplers; and resorcinol, 2-methylresorcinol and 4-chlororesorcinol as couplers for the brown-blond range.

The preferred developer substances being used are, e.g., 2,5-diaminotoluene, 4-aminophenol and 1,4-diaminobenzene, however, 2,5-diaminoanisol, 2,5-diaminobenzyl alcohol and 2-(β-hydroxyethyl)-1,4-diaminobenzene have also achieved a certain importance. In certain cases, tetraaminopyrimidine can also be used as a developer substance.

There are numerous special requirements that oxidizing coloring materials which are used for coloring human hair must meet. They must, for example, be generally recognized as safe in toxicological and dermatological respects and must make it possible to achieve coloring to the desired intensity. Moreover, it is a requirement that a wide range of various nuances of color be able to be produced by means of combining suitable developer and coupler substances. In addition, the attainable hair colorings are required to be favorably light fast, permanent wave fast, acid fast and friction fast. However, in all instances such hair colorings must also remain stable over a period of at least four to six weeks without being affected by light, chemical agents or friction.

While the system comprising the aforesaid developer and coupler substances, which is currently being used in hair coloring agents, meets the stated requirements in terms of those features relating to application technology, it does not satisfy the demands relating to toxicity. Furthermore, it is also desirable that compounds used in hair coloring systems not be mutagenic, or only slightly mutagenic, in commercially known testing methods such as those of B. N. Ames.

Accordingly, it is an object of the present invention to provide hair coloring agents based upon new coupler substances which, inter alia, allow for a wide range of various nuances of colorings that are stable for an extended period of time without being adversely affected by light, chemical agents and friction and which have a high toxicological level of safety.

This and other related objects are achieved according to the compounds of the present invention. In particular, it has been found, very surprisingly, that the toxicological characteristics of certain coupling components conventionally applied in oxidizing hair coloring agents can be substantially improved by means of introducing the tetrafluoroethoxy group into these compounds.

The present invention, therefore, provides agents for the oxidative coloring of hair having a combination of developer and coupler substances in which such agents contain, as the coupler substance, a diaminotetrafluoroethoxybenzene compound, or its acid addition salt, of the general formula I.

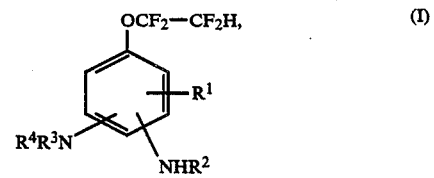

wherein, $R^1$ represents hydrogen or an alkyl group having 1 to 4 carbon atoms; and $R^2$, $R^3$, and $R^4$ independently of one another, represent hydrogen, an alkyl group having 1 to 4 carbon atoms or mono- or dihydroxy alkyl groups having 1 to 4 carbon atoms, provided that the amino groups are situated relative to one another in an ortho- or meta-position.

The coupler substances of the present invention, having physiologically favorable characteristics, above all, have a lower level of mutagenicity than structurally similar non-fluorinated compounds. Moreover, the improvement demonstrated by the compounds of the present invention relative to the corresponding trifluoroethoxy compounds is also particularly surprising and unexpected.

In addition, a comparison, described below, of the coupler substances of the present invention, in which $R^1$ is an alkyl group, shows a distinct improvement of the light fastness for those compounds alkylated in the nucleus relative to those compounds wherein $R^1$ is a hydrogen atom. The light fastness can likewise be improved by substituting the nitrogen atom. Those compounds of formula I in which at least one of the substituents designated $R^1$ to $R^4$ is an alkyl or hydroxy alkyl group are, therefore, particularly well-suited for use in the hair coloring agents according to the invention. The substituents methyl and hydroxyethyl being particularly preferred. With respect to the positioning of the amino groups, those compounds in which the amino groups are in a meta-position relative to one another are preferred.

The following table shows the results of the mutagenicity test according to B. N. Ames (B. N. Ames, J. MacCann and E. Yamasaki, Mut. Res. 31 347–363 (1975)) for two of the coupler substances of formula I in comparison to the known coupler substances, 2,4-diaminotrifluoroethoxybenzene, 2,4-diaminophenetol and 2,4-diaminoanisol.

TABLE

Ames test results of 2,4-diaminoalkoxy benzene derivatives

| Substance | Salmonella thyphimurium strains without (−) and with (+) S9 - Mix | | | | | |
|---|---|---|---|---|---|---|
| | TA 97 | | TA 98 | | TA 100 | |
| | − | + | − | + | − | + |
| 2,4-diamino-5-tetrafluoroethoxy-toluene | − | − | − | − | − | − |
| 2,4-diaminotetra- | − | (+) | − | + | − | − |

TABLE-continued
Ames test results of 2,4-diaminoalkoxy benzene derivatives

| | Salmonella thyphimurium strains without (−) and with (+) S9 - Mix | | | | | |
|---|---|---|---|---|---|---|
| | TA 97 | | TA 98 | | TA 100 | |
| Substance | − | + | − | + | − | + |
| fluoroethoxy-benzene | | | | | | |
| 2,4-diaminotri-fluoroethoxy-benzene | − | − | − | ++ | − | (+) |
| 2,4-diaminophenetol | − | + | − | ++ | − | − |
| 2,4-diaminoanisol | − | + | − | 30 + | − | (+) | no back mutation: −
slight back mutation: (+)
increasing back mutation: +, ++

The coupler substances of formula I are new, with the exception of the compound 2,4-diaminotetrafluoroethoxybenzene which is described in the Russian Pat. No. 537 504 as a starting compound for the production of polyamides.

Thus, the present invention also relates to new diaminotetrafluoroethoxybenzene compounds, and their acid addition salts, of general formula I, wherein, $R^1$ represents hydrogen or an alkyl group having 1 to 4 carbon atoms and $R^2$, $R^3$ and $R^4$ represent, independently of one another, hydrogen, an alkyl group having 1 to 4 carbon atoms or mono- or dihydroxy alkyl groups having 1 to 4 carbon atoms, provided that the amino groups are situated relative to one another in an ortho- or meta-position, and $R^1$ through $R^4$ do not simultaneously signify hydrogen when the amino groups are arranged in a 2,4-position.

Processes for the production of several of the inventive diaminotetrafluoroethoxy couplers is described in the following examples which are presented solely for purposes of illustration and not of limitation. In general, the compounds alkylated at the nitrogen atom were produced by dinitrating the compounds of general formula II,

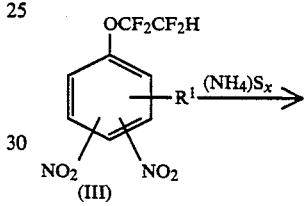

wherein, $R^1$ stands for hydrogen or an alkyl group having 1 to 4 carbon atoms, followed by the subsequent reduction of the dinitro compound III. The reduction can be carried out catalytically with hydrogen or with inorganic reducing agents.

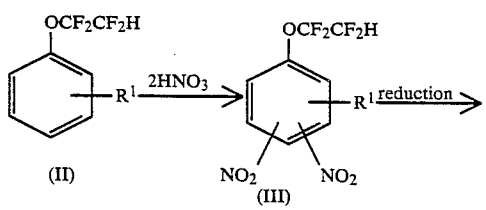

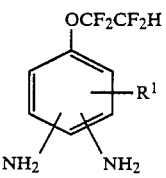

In order to produce the dinitro compounds one can also, of course, start from the mononitro aromatics occurring in the mononitration of II.

The dinitro compounds, III, can serve as starting material for the derivatives alkylated at the nitrogen atom. The careful reduction of a nitro group, e.g., with ascorbic acid or ammonium polysulfide, produces the nitroaniline derivative IV which is also accessible from II by means of mononitration, reduction and a second nitration. Further reaction of the nitroaniline derivative IV by means of alkylation and reduction produces the derivatives of the compounds according to formula I which are alkylated at the nitrogen atom.

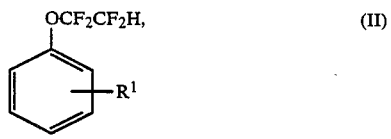

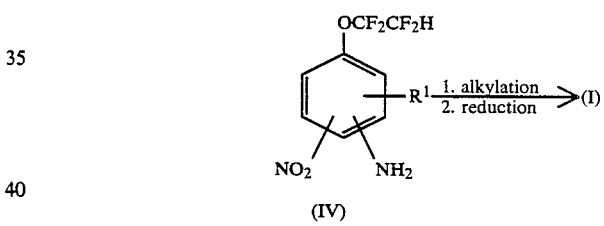

A special method for producing the mono-N-β-hydroxyethyl compounds results from the mononitro compounds produced in the nitration of II, its reduction, reaction with chloroformic acid chloroethylester and subsequent nitration, reduction and dissociation of the oxazolinon according to the following reaction scheme:

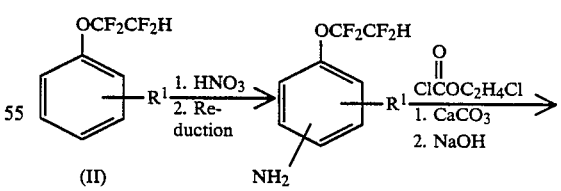

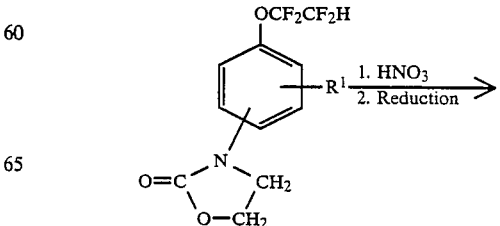

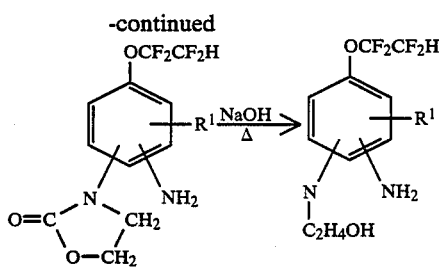

In addition, the compounds alkylated at the nitrogen atom can also be produced from the free amines, in a known manner by means of alkylation, by applying conventional N-alkylation methods as illustrated in the following examples.

The acid addition salts of the compounds of formula I are obtainable by means of reaction with the corresponding organic or inorganic acids.

The coupler substances of formula I are to be used in hair coloring agents in either a free base form or in the form of their physiologically compatible salts with inorganic or organic acids, e.g., as chlorides, sulfates, phosphates, acetates, propionates, lactates or citrates. The compounds of formula I are easily soluble in water and, moreover, have an excellent storage stability, particularly as a component part of the hair coloring agents described herein.

In the hair coloring agents, the coupler substances of formula I are to be contained in a concentration of 0.01 to 3.0% by weight, preferably, 0.1 to 2.0% by weight.

While the coupler substances of formula I are generally employed in approximately equimolar quantities with reference to the developer substances used, it is not disadvantageous if the coupler substances are applied with a certain excess or deficiency. It is also not necessary that the developer components and the coupler components each be homogeneous compounds; rather, the developer components can be a mixture of known developer substances while the coupler components can be a mixture of the compounds according to the present invention and known coupler substances. Examples of known coupler substances that can be contained in the hair coloring agents include, in particular, resorcinol, 4-chlororesorcinol, 2-methylresorcinol, 2-amino-4-($\beta$-hydroxyethylamino)-anisol, 2,4-diamino-phenylethanol, 2,4-diamino-phenoxyethanol, 1,5-dihydroxytetraline, m-aminophenol, 3-amino-2-methylphenol, 3-amino-6-methylphenol, 4-hydroxyl-1,2-methylenedioxybenzene, 4-amino-1,2-methylenedioxybenzene, 2,4-diaminoanisol and 2,4-diaminophenetol.

Of the known developer substances mainly 1,4-diaminobenzene, 2,5-diaminotoluene, 2,5-diaminoanisol, 2,5-diaminobenzyl alcohol, 3-methyl-4-aminophenol and 4-aminophenol come under consideration as component parts in the hair coloring agents of the present invention.

The total quantity of the developer substance-coupler substance combination contained in the hair coloring agents described herein should amount to approximately 0.1 to 5.0% by weight, preferably 0.5 to 3.0% by weight, of the hair coloring agents of the present invention.

In addition, in order to achieve certain color nuances conventional direct dyeing coloring materials can also be contained, e.g., triphenylmethane dyes, such as, Diamond Fuchsine (C.I. 42,510) and Leather Ruby HF (C.I. 42,520); aromatic nitro dyes, such as 2-amino-4,6-dinitrophenol, 2-nitro-1,4-diaminobenzene, 2-amino-4-nitrophenol and 2-amino-5-nitrophenol; and azo dyes, such as, Acid Brown 4 (C.I. 14,805), as well as anthraquinone dyes such as 1,4-diaminoanthraquinone.

In addition, the claimed hair coloring agents can also contain self-coupling preliminary coloring stages, such as, e.g., 2-amino-5-methylphenol, 2-amino-6-methylphenol, 2-amino-5-ethoxyphenol or 2-propylamino-5-aminopyridine.

Of course, the coupler and developer substances, as well as other coloring components, insofar as they are bases, can be used in the form of physiologically compatible acid addition salts, for example, as hydrochlorides or sulfates or—insofar as they possess aromatic OH groups—in the form of salts with bases, for example, as alkali phenates.

Moreover, other conventional cosmetic additives can be present in the hair coloring agents, for example, antioxidants such as ascorbic acid or sodium sulfite, perfume oils, complexing agents, wetting agents, emulsifiers, thickeners, conditioning materials, etc.

The preparation form can be, e.g., a solution, particularly an aqueous or aqueous alcohol solution. However, particularly preferred preparation forms are creams, gels or emulsions.

The composition of the hair coloring agents is a mixture of coloring material components with the usual additives for such preparations.

Conventional additives in solutions, creams, emulsions or gels are, for example, solvents such as water, lower aliphatic alcohols, e.g., ethanol, propanol and isopropanol, as well as polyhydric alcohols such as ethylene glycol, 1,2-propylene glycol and glycerin, in addition to wetting agents or emulsifiers of the classes of anionic, cationic, amphoteric or non-ionogenic surface-active substances such as fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides, ethoxylated fatty acid esters, and thickeners, such as, higher fatty alcohols, bentonite, starch, polyacrylic acid, cellulose derivatives, alginates, Vaseline, paraffin oil and fatty acids, as well as conditioning materials such as lanolin derivatives, cholesterol, pantothenic acid and betaine. These component parts are used in quantities usual for such purposes, for example, the wetting agents and emulsifiers can be contained in concentrations of approximately 0.5 to 30% by weight, while the thickeners can be contained in the preparation in quantities of approximately 0.1 to 25% by weight.

Depending on the particular composition, the hair coloring agents of the invention can react in a slightly acidic, neutral or alkaline manner. In particular, they have a pH value in the alkaline range of 8.0 to 11.5, wherein adjustment is preferably effected with ammonia. But organic amines, for example, monoethanolamine and triethanolamine, or inorganic bases, e.g., sodium hydroxide and potassium hydroxide, can also be used.

For application in the oxidative coloring of hair the above-mentioned hair coloring agents are mixed immediately before use with an oxidizing agent and an amount of the mixture sufficient for the hair coloring treatment, generally in the range of approximately 60 to 200 g, depending on the quantity of hair, is applied to the hair.

Hydrogen peroxide, in particular, is taken into consideration as an oxidizing agent for developing the hair coloring, for example, as a 6% aqueous solution or its addition compounds in urea, melamine or sodium borate. The mixture is then allowed to act on the hair at 15° to 50° C. for approximately 10 to 45 minutes, preferably 30 minutes. The hair is then immediately rinsed with water and dried. After rinsing, the hair is possibly washed with a shampoo and rerinsed with a weak, physiologically compatible organic acid, e.g., citric acid or tartaric acid.

With respect to the coloring possibilities, the hair coloring agents, according to the invention, offer a wide selection of various color nuances, dependent upon the type and composition of the coloring components employed. The colorings may range from blonde, brown, ash, mat, and golden to blue color tones. The color tones are characterized by a good intensity of color and sufficient light fastness.

Finally, it is also possible, with the aid of the hair coloring agents employing the present invention, to tint graying, chemically undamaged hair with good covering power.

The invention will now be more fully described by the following examples. It should, however, be noted that such are given by way of illustration and not of limitation. Unless otherwise indicated, all percentages in the following Examples represent percentages by weight.

PRODUCTION EXAMPLES

Example 1: 2,4-diaminotetrafluoroethoxybenzene

Step 1: 2,4-dinitrotetrafluoroethoxybenzene production 6 g (0.025 moles) of 2-nitrotetrafluoroethoxybenzene or 4-nitrotetrafluoroethoxybenzene are dissolved in 20 ml concentrated sulfuric acid (density, d=1.84 g/ml) and nitrated at 5°-10° C. with a mixture of 1.2 ml nitric acid (d=1.5 g/ml) and 5 ml sulfuric acid (d=1.84 g/ml). After the addition of the nitrating acid, the aforesaid preparation is allowed to heat at room temperature. The preparation, after being left to stand overnight, is then poured onto ice water. The precipitated oil is separated by means of decanting and the aqueous phase is extracted three times with 50 ml ether. The ether extracts and the oil are then combined, washed with sodium bicarbonate solution so as to be acid-free and dried over calcium chloride. After distilling the solvent, 6.6 g (93% of the theoretical yield) dinitro compound (from the 2-nitrotetrafluoroethoxybenzene) or 6.7 g (94% of the theoretical yield) dinitrotetrafluoroethoxybenzene (from the 4-nitrotetrafluoroethoxybenzene) is obtained. The dinitro compound was further processed directly in the following step without further purification.

Step 2: 2,4-diaminotetrafluoroethoxybenzene production 89 g (0.31 moles) 2,4-dinitrotetrafluoroethoxybenzene, according to Step 1, 125 ml of a 50% aqueous solution of ethanol and 106.5 g iron powder (1.91 moles) are heated to 60°-70° C. in a water bath in a three-necked flask, which is equipped with a reflux condensor, drop addition funnel, stirrer and internal thermometer. Next, a solution of 6.5 ml concentrated hydrochloric acid in 30 ml 50% aqueous solution of ethanol is added dropwise so that the reduction takes place accompanied by reflux and gentle boiling. When the addition is terminated it is then stirred for 2 hours accompanied by reflux, allowed to cool and neutralized with alcoholic potassium hydroxide. Unconverted iron and iron oxides are vacuum filtrated, accompanied by rewashing with ethanol. The solution is concentrated and the residue is distilled in the vacuum. 40 g (57% of the theoretical yield) of the free base is obtained which has a boiling range of 114°-117° C. at 106 Pascal. This product can be transformed into dihyrochloride with hydrochloric acid.

| ANALYSIS (dihydrochloride) | | |
|---|---|---|
| | calculated | found |
| C | 32.34% | 32.78% |
| H | 3.39% | 3.41% |
| N | 9.42% | 9.78% |
| Cl | 23.86% | 24.16% |

Example 2:
2,4-bis-[(2'-hydroxylethyl)-amino]-tetrafluoroethoxybenzene

Step 1:
2,4-bis-(2'-chloroethoxycarbamido)-tetrafluoroethoxybenzene production 2.47 g (8.3 mmoles) 2,4-diaminotetrafluoroethoxybenzenedihydrochloride of Example 1 are dissolved in 10 ml dioxane and heated for 1 hour to 90° C. with 2 g calcium carbonate and 4.3 g (30 mmoles) chloroformic acid chloroethylester.

This mixture is then poured onto ice with the residue being filtered off, dried and then used without further purification in Step 2.

Step 2:
2,4-bis-[(2'-hydroxylethyl)-amino]-tetrafluoroethoxybenzene production 3.5 g (8.0 mmoles) of the dicarbamates from Step 1 are heated in 20 ml 20% aqueous sodium hydroxide solution for 1 hour to 120° C. (bath temperature), cooled, then extracted with ethyl acetate. The combined ethyl acetate phases are washed once with water and dried over sodium sulfate. The solvent is then evaporated in a vacuum with the residue being transformed into dihydrochloride. The dihydrochloride, with a melting point of 145° C., be recrystalized from methyl ethyl ketone.

| ANALYSIS | calculated | found |
|---|---|---|
| C | 37.41% | 37.87% |
| H | 4.71% | 4.81% |
| N | 7.27% | 7.34% |
| Cl | 18.40% | 17.94% |

For all of the following NMR spectrums: All data in δ [ppm] Standard: tetramethylsilane s=singlet, d=doublet, t=triplet, m=multiplet NMR spectrum (in DMSO-$d_6$);

8.2-7.4 (wide, $NH_3^{\oplus}$, OH, when the sample is agitated with $D_2O$ the signal disappears), 7.27 (d, J=8 Hz, 6-H), 7.12 (t, J=52 Hz, three signals at 7.64, 7.12 and 6.60 ppm again form triplets with J=4 Hz, $CF_2CHF_2$), 7.04 (d, J=2 Hz, 3-H), 6.83 (dd, $J_1$=8 Hz, $J_2$=2 Hz, 5-H), 3.8-3.5 (m, —$CH_2OH$), 3.5-3.1 (m, —$CH_2NH$—).

Example 3: 3,4-diaminotetrafluoroethoxybenzene

Step 1: 4-acetylaminotetrafluoroethoxybenzene production 23.9 g (0.1 moles) 4-nitrotetrafluoroethoxybenzene are dissolved in 75 ml glacial acetic acid and reduced at 50°–60° C. in the presence of platinum with hydrogen at normal pressure. After receiving 7.4 l hydrogen the catalyst was filtered off and the filtrate is heated 1 hour with 75 ml acetic anhydride accompanied by reflux. The reaction mixture is then concentrated in a vacuum to ⅓ the original solvent quantity and poured onto 1 l ice water. The acetyl amino compound first precipitates as an oil which crystalizes overnight. 23.5 g (94% theoretical yield) of almost colorless crystals with a melting range of 114°–115° C. are obtained.

Step 2: 4-amino-3-nitrotetrafluoroethoxybenzene production 18.8 g (0.08 moles) 4-acetylaminotetrafluoroethoxybenzene of Step 1 are dissolved, accompanied by ice cooling at 0° C., in 150 ml concentrated sulfuric acid. Nitration is carried out at the same temperature with a mixture of 10.3 ml (0.15 moles) concentrated nitric acid (d=1.4 g/ml) and 10 ml concentrated sulfuric acid. After standing overnight this mixture is poured onto approximately 500 g ice. A viscous oil precipitates. The oily phase is decanted and repeatedly washed with water. The oil is made to solidify by means of cooling and scraping. It is, according to DC, a mixture of acetylaminonitro- and aminonitro-compounds. It is then saponfied by means of dissolving and boiling, with reflux, with methanol and concentrated hydrochloric acid and then neutralized with ammonia. The 4-amino-3-nitrotetrafluoroethoxybenzene precipitates. Yellow crystals with a melting point of 78° C. were obtained. Yield: 13.4 g (67% of the theoretical yield)

Step 3: 3,4-diaminotetrafluoroethoxybenzene production 12.7 g (0.05 moles) 4-amino-3-nitrotetrafluoroethoxybenzene from Step 2 is dissolved in 100 ml ethanol and catalytically reduced in the presence of platinum at 50° C. with hydrogen at normal pressure. After receiving 3.6 l hydrogen, the catalyst is filtered off and 10 ml concentrated hydrochloric acid is added to the alcoholic solution. It is steamed dry and completely dried in the vacuum dessicator over potassium hydroxide. Yield: 12.5 g (84.5% of the theoretical yield) of 3,4-diaminotetrafluoroethoxybenzene dihydrochloride. The resulting substance is in the form of red-brown crystals which are recrystalized from ethanol/HCl. Melting (decomposition) range 198°–200° C. HCL content, potentiometrically determined: 23.80%. Calculated value: 24.57%.

Example 4: 3-amino-4-(2'-hydroxylethyl)-aminotetrafluoroethoxybenzene

Step 1: 2-chloroethyl-N-(4'-tetrafluoroethoxyphenyl)carbamate production 41.8 g (0.20 moles) 4-aminotetrafluoroethoxybenzene (obtained from the process disclosed in Example 3, Step 1, without acetylation step) is dissolved in 100 ml dioxane. 12.0 g calcium carbonate and 31.4 g (0.22 moles) chloroformic acid chloroethylester are added and heated for 30 minutes to 90° C. This mixture is then poured onto ice with the residue being filtered off and recrystalized from methanol/water. Colorless crystals having a melting range of 114°–116° C. were obtained in almost a quantitative yield.

Step 2:

N-(4'-tetrafluoroethoxyphenyl)-oxazolidin-2-on 62.0 g (0.20 moles) of the carbamate from the first step of this Example is heated for 1 hour in 200 ml 1N sodium hydroxide solution (0.20 moles NaOH). When cooling, a precipitation results which is recrystalized from methanol/water. The oxazolidinon crystalizes in colorless crystals having a melting range of 74°–76° C.

Step 3: N-(2'-nitro-4'-tetrafluoroethoxyphenyl)-oxazolidin-2-on production 2.79 g (10 mmoles) of the oxazolidinon of Step 2 are dissolved in 7 ml concentrated sulfuric acid and nitrated at 0° C. with a mixture of 0.43 ml (10 mmoles) fuming nitric acid and 3.6 ml concentrated sulfuric acid.

The preparation is then poured onto ice so that an oil precipitates which crystalizes within a short time. Slightly yellowish crystals are obtained having a melting point of 83° C.

Step 4: N-(2'-amino-4'-tetrafluoroethoxyphenyl)-oxazolidin-2-on production

The reduction of the nitro compound of Step 3 is carried out catalytically in the presence of platinum with hydrogen at normal pressure. Acetic acid is used as a solvent. After receiving the theoretical hydrogen quantity, the catalyst is filtered off and the solvent is evaporated with a vacuum. The amino compound is obtained in quantitative yield as colorless crystals of melting range 106°–108° C.

Step 5:

The oxazolidinon of Step 4 is dissociated in 20% aqueous sodium hydroxide solution as described in the second step of Example 2. The dihydrochloride, with a melting point of 118° C., is obtained in colorless crystals.

Example 5: 2,4-diamino-3-tetrafluoroethoxytoluene and 2,4-diamino-5-tetrafluoroethoxytoluene

Step 1: 4-nitro-3-tetrafluoroethoxytoluene production 20.8 g (0.10 moles) 3-tetrafluoroethoxytoluene is placed in 25 ml glacial acetic acid and nitrated at 5° C. with a mixture of 30 ml concentrated nitric acid and 35 ml concentrated sulfuric acid. The solution turns yellow as the nitrating acid is added dropwise. When the addition is terminated the cooling bath is removed and the solution is agitated for 3½ hours at room temperature. The solution is then poured onto ice, the precipitated oil separated and the aqueous solution is extracted with ethyl acetate. After drying over sodium sulfate and distilling the solvent, a yellow oil remains in quantitative yield, which according to the NMR spectrum, involves the 4-nitro-3-tetrafluoroethoxytoluene.

NMR (solvent: CDCl$_3$): 8.06 (d, J=10 Hz, 5-H), 7.4–7.1 (m, 2-H and 6-H), 5.93 (t, J=53 Hz, the three signals at 6.82, 5.93, 5.04 again form triplets with J=3 Hz, CF$_2$CHF$_2$), 2.65 (s, CH$_3$)

Step 2: 2,4-dinitro-5-tetrafluoroethoxytoluene and 2,4-dinitro-3-tetrafluoroethoxytoluene production 5.1 g (0.02 moles) of the mononitro compound from Step 1 are dissolved in 5 ml concentrated sulfuric acid and nitrated at 0°–5° C. with a mixture of 7.5 ml fuming nitric acid (d=1.50 g/ml) and 9 ml concentrated sulfuric acid. After adding the nitrating acid, which takes approximately 40 minutes, the ice bath is removed and the preparation is agitated for 24 hours at room temperature. This preparation is then poured onto ice, the precipitated oil is separated immediately and the aqueous phase is extracted with ethyl acetate. After combining the organic phases, the latter are dried over sodium sulfate and the solvent evaporated in a vacuum. 5.4 g (90% of the theoretical yield) of a mixture of the two dinitro compounds is obtained which is separated by means of column chromatography ($SiO_2$, <0.063 mm, eluent: cyclohexane/2% ether).

The two compounds, 2,4-dinitro-3-tetrafluoroethoxytoluene and 2,4-dinitro-5-tetrafluoroethoxytoluene are present in a ratio of 1:3, the 3-tetrafluoroethoxy compound has the higher $R_F$ value. The two dinitro compounds are oils in the pure state.

NMR spectrum of the 2,4-dinitro-3-tetrafluoroethoxytoluene (dissolved in $CDCl_3$): 8.16 (d, J=9 Hz, 5-H), 7.52 (d, J=9 Hz, 6-H, signals widen by coupling with $CH_3$), 5.93 (t, J=53 Hz, the three signals at 6.81, 5.93 and 5.05 ppm again form triplets with J=3 Hz, $CF_2CHF_2$), 2.60 (s, $CH_3$).

NMR spectrum of the 2,4-dinitro-5-tetrafluoroethoxytoluene (dissolved in $CDCl_3$): 8.74 (s, 3-H), 7.52 (s, 6-H, widens by coupling with $CH_3$), 6.05 (t, J=53 Hz, the three signals at 6.92, 6.05 and 5.17 ppm again form triplets with J=4 Hz, $CF_2CHF_2$), 2.81 (s, $CH_3$).

Step 3(a): 2,4-diamino-3-tetrafluoroethoxytoluene production 0.2 g (0.7 mmoles) 2,4-dinitrotetrafluoroethoxytoluene is hydrogenated in 10 ml ethanol with hydrogen at normal pressure in the presence of platinum. After receiving 90 ml hydrogen (theoretical yield: 94 ml) the catalyst is filtered off and the dihydrochloride is produced with HCl. Reddish crystals having a melting (decomposition) point of 180° C. are obtained.

NMR spectrum (in DMSO-$d_6$): 7.2 (m, 5-H, 6-H), 7.2–6.6 (wide, $NH_3\oplus$, the signal disappears when agitated with $D_2O$), 6.66 (t, J=51 Hz, $CF_2CHF_2$; further splitting in triplets of the three signals at 7.50, 6.66 and 5.82 ppm cannot be detected because of strong background noise), 2.10 (s, $CH_3$).

Step 3(b): 2,4-diamino-5-tetrafluoroethoxytoluene production 0.5 g (2 mmoles) 2,4-dinitro-5-tetrafluoroethoxytoluene is hydrogenated in 15 ml ethanol with hydrogen at normal pressure with platinum as a catalyst. After receiving 250 ml hydrogen (theoretical: 268 ml) the catalyst is filtered off and the dihydrochloride is produced with hydrochloric acid. Almost colorless crystals with a melting range of 265°–267° C. are obtained (decomposition; in closed tube).

NMR spectrum (in DMSO-$d_6$): 8.35 (wide, $NH_3\oplus$, the signal disappears when agitated with $D_2O$), 7.12 (s, 3-H, 6-H) 6.90 (t, J=53 Hz, the three signals at 7.79, 6.90 and 6.01 ppm again form triplets with J=4 Hz, $CF_2CHF_2$), 2.25 (s, $CH_3$).

Example 6: 3,5-diamino-2-tetrafluoroethoxytoluene and 4,5-diamino-2-tetrafluoroethoxytoluene Step 1: 3,5-dinitro-2-tetrafluoroethoxytoluene and 4,5-dinitro-2-tetrafluoroethoxytoluene production 2.5 g (10 mmoles) 5nitro-2-tetrafluoroethoxytoluene is added dropwise to a solution of 1.5 g (14.8 mmoles) potassium nitrate in 15 ml concentrated sulfuric acid at room temperature accompanied by agitation. The solution is then heated for 3 hours to 100° C. After cooling, it is poured onto ice and extracted with ethyl acetate. The combined organic phases are washed with water and sodium carbonate solution and dried over sodium sulfate. After distilling the solvent an oil remains which, aside from the two desired nitro compounds, contains a little phenolic by-product. Separation occurs by means of filtration via a short silica gel column (eluent: toluene). The filtrate is concentrated in a vacuum and the residue is analyzed chromatographically with silica gel (<0.063 mm, eluent: cyclohexane/2% ether).

The 3,5-dinitro-2-tetrafluoroethoxytoluene and the 4,5-dinitro-2-tetrafluoroethoxytoluene are obtained in a ratio of 5:4, the m-nitro compound appears first in the column chromatography.

NMR spectrum of the 3,5-dinitro-2-tetrafluoroethoxytoluene (dissolved in $CDCl_3$): 8.66 (d, J=3 Hz, 4-H), 8.45 (d, J=3 Hz, 6-H), 6.07 (t, J=53 Hz, the signals at 6.95, 6.07 and 5.19 ppm again form triplets with J=3.5 Hz, $CF_2CHF_2$), 2.61 (s, $CH_3$).

NMR spectrum of the 4,5-dinitro-2-tetrafluoroethoxytoluene (dissolved in $CDCl_3$): 7.88 (s, 3-H, 6-H), 6.02 (t, J=53 Hz, the signals at 6.90, 6.02 and 5.14 ppm again form triplets with J=2.5 Hz, $CH_2CHF_2$), 2.50 (s, $CH_3$).

Step 2(a): 3,5-diamino-2-tetrafluoroethoxytoluene production 0.5 g (1.7 mmoles) of the 3,5-dinitro-2-tetrafluoroethoxytoluene is hydrogenated in ethanol with platinum as described in Example 5, Step 3(b). The dihydrochloride is obtained in the form of reddish crystals with a melting (decomposition) point of 241° C.

NMR spectrum (in DMSO-$d_6$): 8.5 (wide, $NH_3\oplus$, the signal disappears when agitated with $D_2O$), 6.91 (t, J=53 Hz, the signals at 7.80, 6.91 and 6.02 ppm again form triplets with J=4 HZ, $CF_2CHF_2$), 6.76 and 6.51 (both d, J=3 Hz, 4-H and 6-H, respectively), 2.20 (s, $CH_3$).

Step 2(b): 4,5-diamino-2-tetrafluoroethoxytoluene production 0.4 g (1.3 mmoles) of the 4,5-dinitro-2-tetrafluoroethoxytoluene is hydrogenated as in Step 2(a). Greenish crystals of dihydrochloride are obtained having a melting (decomposition) point of 238° C.

NMR spectrum (in DMSO-$d_6$): 8.9 ($N\oplus H_3$, the signal disappears when agitated with $D_2O$), 7.07 and 7.01 (2 wide singlets, 3-H and 6-H, respectively). 6.82 (t, J=53 Hz, the three signals at 7.70, 6.82 and 5.94 again form triplets with J=3 Hz, $CF_2CHF_2$, 2.10 (s, $CH_3$).

Example 7: 2,3-diamino-4-tetrafluoroethoxytoluene

Step 1: 3-nitro-4-tetrafluoroethoxytoluene production 2.1 g (10 mmoles) 4-tetrafluoroethoxytoluene is placed in 5 ml concentrated sulfuric acid. A solution of 1.01 g (10 mmoles) potassium nitrate in 25 ml concentrated sulfuric acid added to this solution dropwise at 10° C. within 1½ hours and then poured onto ice and extracted with ethyl acetate. The combined organic phases are washed with water, dried over sodium sulfate and the solvent is evaporated in the vacuum. 2.0 g (78% of the theoretical yield) of the mononitro compound is obtained in the form of an almost colorless oil.

NMR spectrum (in $CDCl_3$): 7.85 (s, wide, 2-H), 7.38 and 7.36 (2 singlets, 5-H and 6-H, respectively) 5.90 (t, J=53 Hz, the three signals at 6.78, 5.90 and 5.02 ppm again form triplets with J=3 Hz, $CF_2CHF_2$), 2.62 (s, $CH_3$).

Step 2: 2,3-dinitro-4-tetrafluoroethoxytoluene production 1.5 g (5.9 mmoles) 3-nitro-4-tetrafluoroethoxytoluene is placed in 7.5 ml concentrated sulfuric acid and 0.65 g (6.4 mmoles) potassium nitrate in 3 ml concentrated sulfuric acid is added dropwise at 0° C. After the addition is terminated it is agitated for 2 hours at ice bath temperature and then poured onto ice. The dinitro compound precipitates as an oil and is extracted with ether. The combined ether phases are washed with sodium bicarbonate solution and water and dried over sodium sulfate. When the solvent is distilled the 2,3-dinitro-4-tetrafluoroethoxytoluene remains as a yellow oil which crystalizes after standing for a short time. Yield: 1.55 g (88% of the theoretical yield), melting point: 35° C.

NMR spectrum (in $CDCl_3$): 7.66 (s, 5-H and 6-H), 5.94 (t, J=53 Hz, the three signals at 6.84, 5.94 and 5.04 ppm again form triplets with J=3 Hz, $CF_2CHF_2$), 2.52 (s, $CH_3$).

Step 3: 2,3-diamino-4-tetrafluoroethoxytoluene production 1.55 g (5.2 mmoles) of the 2,3-dinitro-4-tetrafluoroethoxytoluene is hydrogenated at room temperature and normal pressure with platinum as a catalyst in 20 ml glacial acetic acid with hydrogen. After receiving 740 ml hydrogen (theoretical yield: 750 ml) the catalyst is filtered off and the glacial acetic acid is evaporated with a vacuum. The free base is transformed into dihydrochloride in ether with hydrochloric acid. 0.70 g (43% of the theoretical yield) colorless crystals are obtained with a melting range of 153°–154° C.

NMR spectrum (in DMSO-$d_6$): 7.8 (wide, $NH_3^\oplus$, the signal disappears when the sample is agitated with $D_2O$), 6.96 (d, J=9 Hz, 5-H and 6-H, respectively), 6.90 (t, J=53 Hz, the three signals at 7.43, 6.90 and 6.37 ppm again form triplets with J=4 Hz, $CF_2CHF_2$), 2.25 (s, $CH_3$), 6.65 (d, J=9 Hz, 5-H and 6-H, respectively).

EXAMPLES OF HAIR COLORING AGENTS

Example 8: Hair coloring agent in gel form

| | |
|---|---|
| 1.00 g | 2,4-diaminotetrafluoroethoxybenzene-dihydrochloride produced according to Example 1 |
| 0.75 g | 2,5-diaminotoluene sulfate |
| 0.30 g | ascorbic acid |
| 1.00 g | hydroxylethyl cellulose, highly viscous |
| 5.00 g | lauryl alcohol diglycolethersulfate, sodium salt (28% aqueous solution) |
| 81.95 g | water |
| 100.00 g | |

50 g of the above hair coloring agent is mixed with 50 ml hydrogen peroxide 6% aqueous solution shortly before use and the mixture is then applied to white human hair. After an acting time of 30 minutes at approximately 40° C., the hair is rinsed with water and dried. The hair is colored deep blue.

Example 9: Hair coloring agent in cream form

| | |
|---|---|
| 0.50 g | 3,5-diamino-2-tetrafluoroethoxytoluene dihydrochloride produced according to Example 6(a) |
| 0.20 g | p-phenylene diamine |
| 0.30 g | sodium sulfite, anhydrous |
| 3.50 g | lauryl alcohol diglycolethersulfate, sodium salt (28% aqueous solution) |
| 15.00 g | cetyl alcohol |
| 5.00 g | ammonia, 22% aqueous solution |
| 75.50 g | water |
| 100.00 g | |

50 g of this hair coloring agent is mixed with 30 ml hydrogen peroxide 6% aqueous solution shortly before use and the mixture is then applied to blond human hair. After an acting time of 20 minutes at 40° C., the hair is first rinsed with water and then immediately rinsed with a diluted citric acid solution and finally dried. The hair is colored red.

Example 10: Hair coloring agent in gel form

| | |
|---|---|
| 2.00 g | 2,4-bis—[(2'-hydroxylethyl)-amino]—tetrafluoroethoxybenzene dihydrochloride produced according to Example 2 |
| 1.30 g | 2,5-diaminobenzyl alcohol sulfate |
| 0.30 g | ascorbic acid |
| 15.00 g | oleic acid |
| 7.00 g | isopropanol |
| 10.00 g | ammonia, 22% aqueous solution |
| 64.40 g | water |
| 100.00 g | |

Shortly before using, 50 g of this hair coloring agent are mixed with 50 ml hydrogen peroxide solution (3% aqueous solution) and the mixture is allowed to act on white human hair for 30 minutes at 40° C. The hair is then rinsed with water and dried. The hair has obtained an intensive violet-blue coloring.

Example 11: Hair coloring agent in gel form

| | |
|---|---|
| 2.5 g | 2,4-diamino-5-tetrafluoroethoxytoluene dihydrochloride produced according to Example 5 |
| 0.5 g | 3,5-diamino-2-tetrafluoroethoxytoluene dihydrochloride produced according to Example 6 |
| 4.0 g | p-toluylene diamine sulfate |
| 1.0 g | resorcinol |
| 0.3 g | ascorbic acid |
| 1.0 g | hydroxyethylcellulose, highly viscous |
| 5.0 g | lauryl alcohol diglycolethersulfate, sodium salt (28% aqueous solution) |
| 10.0 g | ammonia, 22% aqueous solution |
| 75.7 g | water |
| 100.0 g | |

50 g of the above hair coloring agent are mixed with 50 ml hydrogen peroxide 6% aqueous solution shortly before use and the mixture is then applied to white human hair. After an acting time of 30 minutes at 40° C., the hair is rinsed with water and dried. The hair is colored black.

Example 12: Hair coloring agent in the form of an aqueous solution

| | |
|---|---|
| 0.50 g | 3,4-diaminotetrafluoroethoxybenzene dihydrochloride produced according to Example 3 |
| 0.50 g | 3-amino-4-(2'-hydroxylethyl)-aminotetra- |

-continued

| | |
|---|---|
| | fluoroethoxybenzene dihydrochloride produced according to Example 4 |
| 2.00 g | p-toluylene diamine sulfate |
| 0.40 g | resorcinol |
| 10.00 g | ethanol, 96% aqueous solution |
| 10.00 g | ammonia, 25% aqueous solution |
| 5.00 g | lauryl alcohol diglycolethersulfate, sodium salt (28% aqueous solution) |
| 71.60 g | water |
| 100.00 g | |

25 g of the above hair coloring agent are mixed with 25 ml hydrogen peroxide 6% aqueous solution shortly before use and the mixture is then applied to white human hair. After an acting time of 45 minutes at 35° C., the hair is rinsed with water and a diluted citric acid solution and dried. The hair is tinted in a natural blond tone.

While only several embodiments and examples of the present invention have been shown and described, it is obvious that many changes and modifications may be made thereunto, without departing from the spirit and scope of the invention.

What is claimed is:

1. A composition for the oxidative coloring of hair, comprising:
   a developer component; and
   at least one coupler component selected from the group consisting of a compound of the formula:

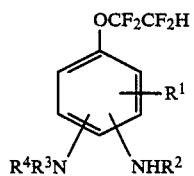

wherein,
   $R^1$ represents a substituent selected from the group consisting of hydrogen and an alkyl having from 1 to 4 carbon atoms; and
   $R^2$, $R^3$, $R^4$ represent the same or different substituents independently selected from the group consisting of hydrogen, an alkyl having from 1 to 4 carbon atoms, a monohydroxyalkyl having from 1 to 4 carbon atoms and a dihydroxyalkyl having from 1 to 4 carbon atoms, provided that the amino groups are situated relative to one another in a positioning selected from the group consisting of ortho- and meta-,
   and the acid addition salts of said compound.

2. The composition according to claim 1, wherein the amino groups of said coupler component are arranged in a meta-position relative to one another.

3. The composition according to claim 1, wherein $R^1$ of said coupler component is an alkyl having from 1 to 4 carbon atoms.

4. The composition according to claim 1, wherein $R^1$, is an alkyl having from 1 to 4 carbon atoms; and $R^2$, $R^3$ and $R^4$ of said coupler component are independently selected substituents selected from the group consisting of an alkyl having from 1 to 4 carbon atoms and an hydroxyalkyl having from 1 to 4 carbon atoms.

5. The composition according to claim 4, wherein $R^1$, is methyl and $R^2$, $R^3$ and $R^4$ of said coupler component are independently selected substituents selected from the group consisting of methyl and hydroxyethyl.

6. The composition according to claim 1, wherein said coupler component has at least one of the radicals, $R^2$ and $R^3$, as hydroxyethyl.

7. The composition according to claim 1, wherein said coupler component is at least one member selected from the group consisting of 2,4-diaminotetrafluoroethoxybenzene, 2,4-bis-(2'-hydroxyethyl)-amino-tetrafluoroethoxybenzene, 3,5-diamino-2-tetrafluoroethoxytoluene, 2,4-diamino-5-tetrafluoroethoxytoluene, 3,4-diaminotetrafluoroethoxybenzene and 3-amino-4-(2'-hydroxyethyl)-aminotetrafluoroethoxybenzene.

8. The composition according to claim 1, wherein said coupler component is 0.01–3.0% by weight of said oxidative hair coloring composition.

9. The composition according to claim 1, wherein said developer component is at least one member selected from the group consisting of 1,4-diaminobenzene, 2,5-diaminotoluene, 2,5-diaminoanisol, 2,5-diaminobenzyl alcohol, 3-methyl-4-aminophenol and 4-aminophenol.

* * * * *